United States Patent
Commereuc et al.

(10) Patent No.: US 6,916,448 B2
(45) Date of Patent: Jul. 12, 2005

(54) PROCESS FOR SELECTIVE PRODUCTION OF PROPYLENE FROM HYDROCARBON FRACTIONS WITH FOUR CARBON ATOMS

(75) Inventors: Dominique Commereuc, Meudon (FR); Christine Travers, Rueil Malmaison (FR)

(73) Assignee: Institut Francais du Petrole, Rueil-Malmaison (FR)

( * ) Notice: Subject to any disclaimer, the term of this patent is extended or adjusted under 35 U.S.C. 154(b) by 5 days.

(21) Appl. No.: 10/682,980

(22) Filed: Oct. 14, 2003

(65) Prior Publication Data

US 2004/0077909 A1 Apr. 22, 2004

Related U.S. Application Data

(60) Division of application No. 09/846,690, filed on May 2, 2001, now Pat. No. 6,743,958, which is a continuation-in-part of application No. 09/745,728, filed on Dec. 26, 2001, now abandoned.

(30) Foreign Application Priority Data

Dec. 24, 1999 (FR) ............................................ 99 16506

(51) Int. Cl.$^7$ ............................. B01J 8/00; B01J 10/00; C07C 2/00; C07C 2/02
(52) U.S. Cl. ........................ 422/134; 422/131; 422/134; 422/187; 422/188; 585/518; 585/520
(58) Field of Search ................................. 422/131, 132, 422/134, 187, 188; 585/326–327, 329, 518, 520, 524, 525, 532, 643–644

(56) References Cited

U.S. PATENT DOCUMENTS

| | | | | |
|---|---|---|---|---|
| 5,962,750 A | * | 10/1999 | Cameron et al. | 568/697 |
| 6,075,173 A | * | 6/2000 | Chodorge et al. | 585/324 |
| 6,207,115 B1 | * | 3/2001 | Chodorge et al. | 422/134 |

* cited by examiner

*Primary Examiner*—Alexa Doroshenk
(74) *Attorney, Agent, or Firm*—Millen White Zelano & Branigan P.C.

(57) ABSTRACT

For the selective production of propylene from an olefinic $C_4$ fraction, a process is implemented that successively comprises:
1) the selective hydrogenation of butadiene with isomerization of butene-1 into butene-2;
2) the separation by distillation of a mixture that is rich in isobutene and butene-1 at the top and a fraction that is rich in butene-2 at the bottom;
3) the skeletal isomerization of isobutene into n-butenes on the top fraction, with recycling in stage 1; and
4) the metathesis of the butene-2-rich fraction with ethylene.

The advantage of this process is to produce in a very selective way polymerization-quality propylene from all of the olefinic compounds of a $C_4$ fraction, including isobutene.

5 Claims, 3 Drawing Sheets

PROCESS FOR SELECTIVE PRODUCTION OF PROPYLENE FROM HYDROCARBON FRACTIONS WITH FOUR CARBON ATOMS

CROSS-REFERENCE TO RELATED APPLICATION

This is a divisional of U.S. patent application Ser. No. 09/846,690 filed May 2, 2001, now U.S. Pat. No. 6,743,958, which is a continuation-in-part of application Ser. No. 09/745,728, filed Dec. 26, 2000 now abandoned. It is also related to U.S. Pat. No. 6,686,510.

The invention relates to a process for selective production of polymerization-quality propylene from an olefinic $C_4$ fraction.

The steam-cracking of feedstocks that consist of light paraffinic fractions produces the ethylene and the propylene that are necessary to petrochemistry. It also produces a certain number of other heavier products, and in particular a $C_4$ hydrocarbon fraction that contains mainly butadiene-1,3, isobutene, n-butenes and butanes, accompanied by traces of acetylenic hydrocarbons.

The catalytic cracking of heavy hydrocarbon feedstocks produces, alongside gasoline and gasoil fractions that are the main products, lighter products, including a $C_4$ hydrocarbon fraction that contains mainly isobutane, isobutene, n-butenes and butanes, accompanied by small amounts of butadiene-1,3 and acetylenic hydrocarbons.

Until recently, only butadiene-1,3 and isobutene were used in the polymer industry, in particular in the tire industry. The increase of the longevity of tires and a relative stagnation of the demand ensure that there is now excess butadiene that is not used or is poorly used. To date, isobutene was used, for example, for the synthesis of ethers with the use of additives in automobile fuels or as a monomer in the synthesis of polyisobutene. These uses, however, can lead to saturation and render the isobutene useless.

This invention proposes a process for treatment of a $C_4$ hydrocarbon fraction that contains primarily isobutene, n-butenes, butanes, and butadiene-1,3 in a variable amount that includes the skeletal isomerization of isobutene into n-butenes and that makes it possible to transform all of the $C_4$ unsaturated compounds into propylene that can be used for, for example, polymerization.

The fractions that are treated in the process according to the invention correspond to the $C_4$ fractions of conversion processes. They can correspond to, for example, the crude $C_4$ fraction for steam-cracking, the $C_4$ fraction for steam-cracking after extraction of the butadiene that is commonly called raffinate-1, or the $C_4$ fraction for catalytic cracking.

The relative proportions of ethylene and propylene that are produced in a steam-cracking operation can be modulated to a certain extent by changing the nature of the feedstock and by modifying the operating conditions (the degree of rigor) of the cracking. The operating method that is oriented toward a larger proportion of propylene, however, inevitably entails a decline in the yield of ethylene and a higher $C_4$ fraction and gasoline fraction production.

Another object of this invention is thus to increase the propylene production while maintaining a high ethylene yield with the treatment of the $C_4$ hydrocarbon fraction and therefore without it being necessary to reduce the rigorous conditions of the steam-cracking device.

The process that is the object of the invention is more specifically a process for converting into propylene an olefinic $C_4$ fraction, whereby said fraction comprises diolefins, primarily butadiene-1,3, butene-1, butene-2, isobutene and acetylenic impurities, and whereby said process comprises the following stages that take place successively:

1) the selective hydrogenation of diolefins and acetylenic impurities with isomerization of butene-1 into butenes-2, carried out in a reactor, in the presence of a catalyst, in order to obtain an effluent that contains for the most part butenes-2 and isobutene, and that contains virtually no diolefins or acetylenic compounds;

2) the separation by distillation of a top fraction that contains for the most part isobutene and unconverted butene-1 in the first stage, and a bottom fraction that contains essentially butene-2 and butane; and 4) the metathesis of the butenes-2 fraction that is obtained from stage 2 with the ethylene so as to obtain an effluent that contains propylene, whereby the metathesis is followed by a separation of the propylene;

whereby said process also comprises a stage 3 of skeletal isomerization of the isobutene into n-butenes in the top fraction, with recycling of at least a portion of the effluent in stage 1.

The isomerization of butene-1 into butenes-2 as carried out in stage 1 can also be carried out in part in association with the distillation (stage 2) by using an isomerization catalyst as described for stage 1 according to the teachings of French FR-B-2 755 130, in the name of the applicant.

The special conditions of the different stages of the process according to the invention, carried out from a $C_4$ hydrocarbon fraction that contains primarily isobutene, n-butenes, butanes, as well as butadiene in a variable amount, whereby said $C_4$ fraction is subjected to these stages to produce essentially propylene, are described in more detail below.

The main object of the first stage is to transform the butadiene and the n-butenes into butenes-2. Actually, the butenes-2 are the source of the propylene that is produced in stage 4 of metathesis in the presence of ethylene. It is therefore desirable to maximize the butenes-2 yield, i.e., to draw as close as possible to the ratio that is allowed by thermodynamics. The second object of this stage is to eliminate the acetylenic hydrocarbon traces that are always present in these fractions and that are poisons or contaminants for the subsequent stages.

In this first stage, the following reactions are thus carried out simultaneously in the presence of hydrogen:

the selective hydrogenation of butadiene into a mixture of n-butenes;

the isomerization of butene-1 into butenes-2 to obtain a distribution that is close to the thermodynamic equilibrium; and the selective hydrogenation of the acetylenic hydrocarbon traces into butenes.

These reactions can be carried out with various specific catalysts that comprise one or more metals, for example from group 10 of the periodic table (Ni, Pd or Pt), deposited on a substrate. A catalyst that comprises at least one palladium compound that is fixed on a refractory mineral substrate, for example on an alumina, is preferably used. The palladium content in the substrate can be 0.01 to 5% by weight, preferably 0.05 to 1% by weight. Various pretreatment methods that are known to one skilled in the art optionally can be applied to these catalysts to improve the selectivity in the hydrogenation of butadiene into butenes at the expense of the total hydrogenation of butane that it is necessary to avoid. The catalyst preferably contains 0.05 to 10% by weight of sulfur. Advantageously, a catalyst is used that comprises palladium that is deposited on alumina, and sulfur.

The catalyst can advantageously be used according to the process that is described in Patent FR-B-2 708 596. According to this process, the catalyst is treated, before it is loaded into the hydrogenation reactor, by at least one sulfur-containing compound that is diluted in a solvent, then the catalyst that is obtained that contains 0.05 to 10% by weight of sulfur is loaded into the reactor and activated under a neutral atmosphere or a reducing atmosphere at a temperature of 20 to 300° C., a pressure of 0.1 to 5 MPa and a VVH of 50 to 600 $h^{-1}$, and the feedstock is brought into contact with said activated catalyst.

The use of the catalyst, preferably with palladium, is not critical, but it is generally preferred to use at least one down-flow reactor through a catalyst fixed bed. When the proportion of butadiene in the fraction is large, which is the case, for example, of a steam-cracking fraction when it is not desired to extract the butadiene from it for specific uses, it may be advantageous to carry out the transformation in two reactors in series to better monitor the selectivity of the hydrogenation. The second reactor can have a rising flow and play a finishing role.

In some cases, it may be advisable to dilute the feedstock that is to be treated by said $C_4$ fraction in which the butadiene is partially or totally hydrogenated.

The amount of hydrogen that is necessary for all of the reactions that are carried out in this stage is adjusted based on the composition of the fraction advantageously to have only a slight hydrogen excess relative to the stoichiometry.

The operating conditions are selected such that the reagents and the products are in liquid phase and such that they promote the formation of butenes-2. It may be advantageous, however, to select an operating mode such that the products are partially evaporated at the outlet of the reactor, which facilitates the thermal monitoring of the reaction. The temperature may vary from 0 to 200° C., preferably from 0 to 150° C. or better from 0 to 70° C. The pressure may be adjusted to a value of 0.1 to 5 MPa, preferably 0.5 to 4 MPa and advantageously from 0.5 to 3 MPa, such that the reagents, at least in part, are in liquid phase. The volumetric flow rate may be from 0.5 to 20 $h^{-1}$ and preferably from 1 to 10 $h^{-1}$, with an $H_2$/diolefin molar ratio of 0.5 to 5 and preferably 1 to 3.

The hydroisomerization reactor or reactors may advantageously be followed by a stabilization column that eliminates the traces of gaseous hydrocarbons that are optionally present in the feedstock hydrogen.

The object of the second stage is to separate by distillation the $C_4$ fraction that is obtained from the preceding stage to obtain, on the one hand, a fraction that contains isobutene, isobutane and the majority of butene-1, on the other hand, a fraction that contains a small amount of butene-1, butenes-2 and n-butane. The isobutene that is thus concentrated is conducted to stage 3 of skeletal isomerization. The butenes-2 fraction is directed toward the metathesis stage.

To reduce as much as possible the butene-1 concentration in the effluent of the column head, it is possible to use a reactive distillation column that comprises, on the inside of the column or outside, one or more feedstocks of the catalyst that is used as described for stage 1. The reactive distillation column that is used can then be of any type. In a preferred arrangement, at least one zone that contains the catalyst is arranged. The mechanical arrangement of the catalyst in the catalytic zone or zones should be such that it disturbs the flows of vapor and liquid as little as possible between the two separation zones that frame it. The catalyst can be placed, for example, in a thin layer on perforated plates or on grids, or in bags that are suspended or laid on substrates that ensure their mechanical behavior, or any other way that is known to one skilled in the art. On the other hand, the catalyst can be placed in the column so that only an upward flow of liquid phase passes through it. It can also be arranged in the form of catalytic packing according to the different implementations that are known. The separation zones that frame the catalytic zones can comprise plates or packing.

One of the uses of the column can correspond to, for example, the one that is described in French Patent FR-B-2 755 130 in the name of the applicant.

The distillation top fraction that is rich in isobutene is subjected in stage 3 to a skeletal isomerization that is intended to transform the isobutene into n-butenes, which can be sent to the inlet of zone 1. The optionally present isobutene may be purged.

This skeletal-isomerization reaction can be carried out with catalysts that have an alumina base or more particularly activated or vapor-treated aluminas (U.S. Pat. No. 3,558, 733) or that comprise compounds such as those of titanium (U.S. Pat. No. 5,321,195 of the applicant) and/or boron (U.S. Pat. No. 5,659,104 of the applicant) in the case of eta- or gamma-aluminas, halogenated aluminas (U.S. Pat. No. 2,417,647) or bauxite. Zeolites or molecular sieves that have a mono-dimensional microporous network (Patent Documents EP-A-523 838, EP-A-501 577 and EP-A-740 957 of the applicant) can also constitute active phases of skeletal-isomerization catalysts. The alumina-based catalysts are generally used in the presence of water at temperatures of from 200° C. to 700° C., at a pressure of 0.1 to 2 MPa, at a volumetric flow rate of 0.1 to 20 $h^{-1}$ and with a molar ratio of injected water to hydrocarbon of 0.1 to 10. The zeolitic catalysts are used without water, at a temperature of 200° C. to 500° C., under a pressure of 0.1 to 2 MPa and at a volumetric flow rate of 0.1 to 20 $h^{-1}$.

The skeletal isomerization of the isobutene into n-butenes is carried out preferably with a catalyst that comprises alumina and titanium at a temperature of 300° C. to 570° C., a pressure of 0.1 to 1 MPa, at a volumetric flow rate of 0.1 to 10 $h^{-1}$, and in the presence of water injection, whereby the molar ratio of injected water/olefinic hydrocarbons is 0.1 to 10.

A catalyst that contains alumina and 0.03 to 0.6% by weight of titanium and that can also contain 0.05 to 5% by weight of an oxide of an element of group IIIA, whereby this element advantageously is boron, will preferably be used in the invention. Before being brought into contact with the hydrocarbons of the feedstock, this catalyst advantageously will have undergone a water vapor treatment at a temperature of 120–700° C. under a partial water vapor pressure that is greater than 0.05 MPa, for a period of 0.5 to 120 hours.

The bottom fraction of the distillation zone, rich in butenes-2, preferably contains at most 1% by weight of butene-1, advantageously at most 0.5% by weight, and at most 1% by weight of isobutene. The butenes-2 fraction that is obtained from stage 2 does not contain outside contaminants and can therefore be sent directly into the fourth stage of the process. In this last stage, the butenes-2 are reacted with ethylene to produce propylene by metathesis. Because of the small amount of butene-1 in the feedstock, the by-product formation is very limited.

The metathesis reaction of the ethylene with the butenes-2 can be catalyzed by varied metallic oxides that are deposited on substrates, for example, by molybdenum, tungsten or rhenium oxides. A catalyst that comprises at least one rhenium oxide that is deposited on a substrate that comprises a refractory oxide that itself contains at least alumina and that has an acidic nature, such as, for example, alumina itself, silica-aluminas or zeolites, is preferably used.

It is possible to cite, by way of preferred examples, the catalysts that comprise rhenium heptoxide that is deposited on a gamma-alumina, such as those described in U.S. Pat. No. 4,795,734. The rhenium content (expressed in metallic rhenium) can be 0.01 to 20%, preferably 1 to 15% by weight. The catalysts are subjected to, for example, a final thermal activation at a temperature of 400 to 1000° C. for a period of 10 minutes to 5 hours under a non-reducing atmosphere.

The catalysts that comprise rhenium heptoxide that is deposited on an alumina can also be modified by the addition of an oxide of another metal. Such modified catalysts comprise, for example, rhenium in the oxide state, at a rate of 0.01 to 20% by weight expressed in metallic rhenium, deposited on a substrate that contains at least 75% by weight of alumina and 0.01 to 30% by weight of at least one oxide of a metal that is selected from the group that is formed by niobium and tantalum, as described in Patent FR-B-2 709 125. Another class of modified catalysts comprises rhenium in the oxide state, at a rate of 0.01 to 20% by weight expressed in metallic rhenium, deposited on a substrate that contains at least 75% by weight of alumina and 0.01 to 10% by weight of aluminum of a compound of formula $(RO)_q AlR'_r$, where R is a hydrocarbyl radical of 1 to 40 carbon atoms, R' is an alkyl radical of 1 to 20 carbon atoms, and q and r are equal to 1 or 2, with q+r equal to 3 (see Patent FR-B-2 740 056).

The metathesis reaction is carried out preferably in a liquid phase, without oxygen, oxidized compounds and moisture, and at a temperature of 0 to 200° C., preferably 20 to 150° C., under a pressure at least equal to the vapor pressure of the reaction mixture at the reaction temperature.

The catalyst can be used in a fixed bed. Since it must be regenerated frequently, however, it is then necessary to use at least two reactors in parallel, whereby one is in use while the other is being regenerated. A catalyst moving bed system as described in French Patent FR-B-2 608 595 is preferably used. The catalyst is drawn off at regular time intervals from the bottom of the reactor and transferred to a continuous regeneration system, from where it is sent to the top of the reactor.

Taking into account the limitations that are imposed by thermodynamics, the unconverted ethylene is fractionated in a first distillation column and recycled in the metathesis reactor. A second distillation column separates the propylene and the unconverted $C_4$ hydrocarbons that can be recycled in the metathesis reactor or in another location of the process.

When the process is applied to a steam-cracking $C_4$ fraction, it may be advantageous to integrate the metathesis unit with the cracking device to take advantage of the fractionation train of the latter. The ethylene that is obtained from the steam-cracking operation is then used in the metathesis stage.

The succession of treatments adopted in the process according to the invention has many advantages. The most reactive compounds of the fraction, in particular the butadiene-1,3 that is present in variable amounts, as well as the traces of acetylenic hydrocarbons, are transformed from the first stage and therefore will not be the cause of parasitic reactions in the following stages. Furthermore, the selective hydrogenation of diolefins (butadiene-1,3 and, if necessary, butadiene-1,2) into butenes, the hydroisomerization of butene-1 and the skeletal isomerization of isobutene into n-butenes make it possible to increase considerably the butenes-2 concentration in the fraction, which thereby promotes a high yield of propylene in the metathesis stage.

The fractionation of the fraction that is obtained from the hydroisomerization into isobutene and butene-1, on the one hand, and into butenes-2, on the other hand, makes it possible to concentrate the isobutene for the skeletal-isomerization stage, as well as the butenes-2 that are then subjected to metathesis.

In addition, in the following metathesis stage (stage 4), the low butene-1 content in the butenes-2-rich fraction makes it possible to obtain a propylene selectivity that is close to 100%. Actually, it is known that the butene-1 reacts with the butenes-2 to produce propylene and pentenes, and that it reacts with itself to produce hexenes. Pentenes and hexenes are by-products of low value, which it is necessary to eliminate, in a costly manner. The process therefore makes possible an appreciable increase of the propylene yield and facilitates the recycling of butenes-2 in the metathesis reactor, since there are few pentenes and hexenes to eliminate.

BRIEF DESCRIPTION OF THE DRAWINGS

The invention also relates to an installation (illustrated by FIG. 1) that is used to implement the process that is described above.

Figure 1:
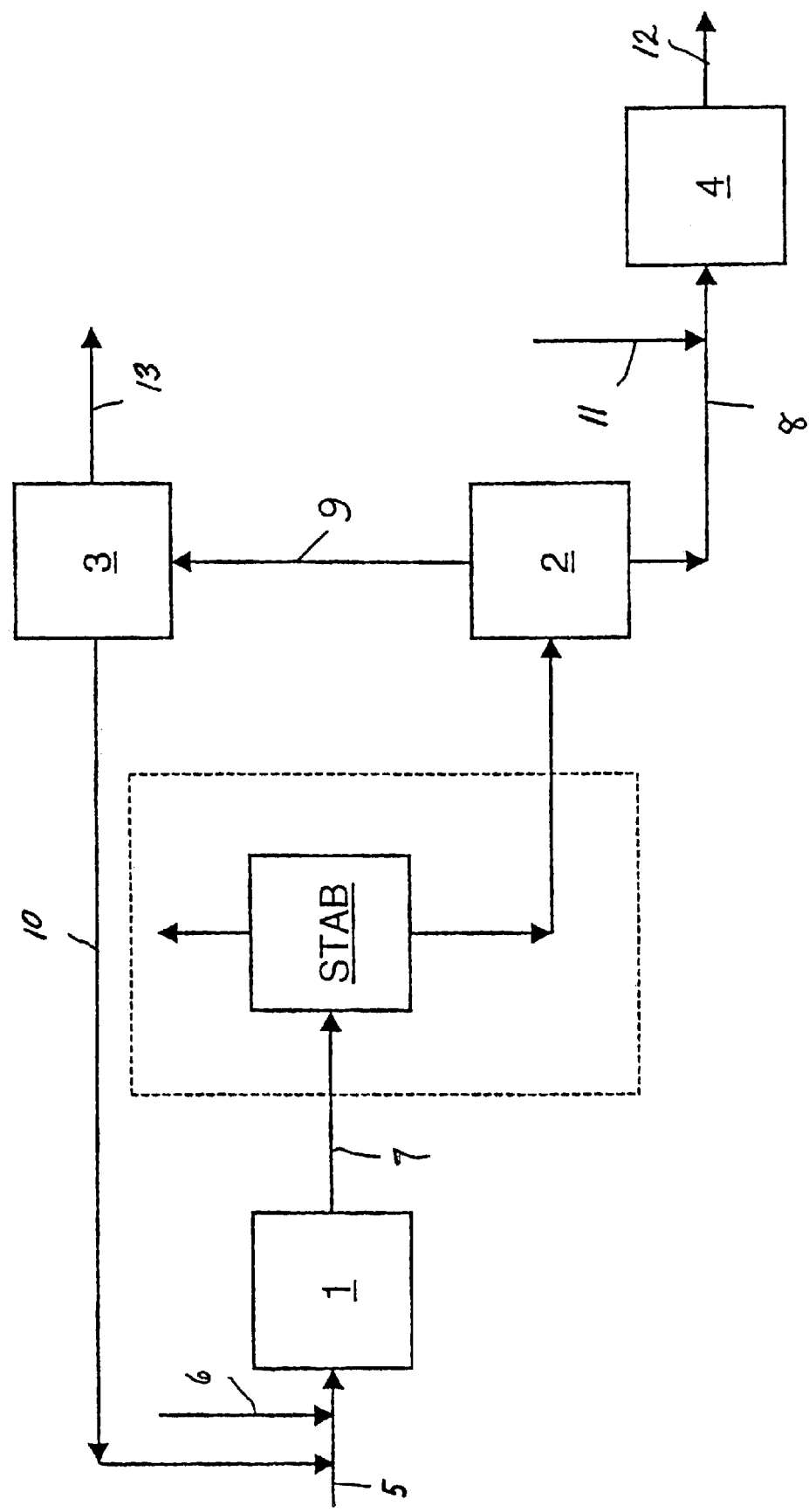
FIG. 1 represents an embodiment of the invention comprising:
  a zone 1 for selective hydrogenation with isomerization of butene-1 into butene-2, whereby said zone comprises at least one means 5 for introducing fraction $C_4$ that is to be converted, at least one means 7 for the output of the effluent and at least one means 6 for the introduction of hydrogen, whereby said zone also comprises at least one catalyst bed;
  a zone 2 for separation that comprises at least one means 7 for the introduction of the effluent that is obtained from zone 1, at least one means 9 for the output of isobutene and butene- 1, at least one means 8 for the output of butene-2 and n-butane; and
  a zone 4 for metathesis that contains at least one catalyst bed and that comprises at least one means 8 for introducing the effluent that is obtained from zone 2, at least one means 11 for introducing ethylene and at least one means 12 for the output of the propylene,
whereby said installation also comprises a skeletal-isomerization zone 3 that comprises at least one means 9 for introducing the effluent that is obtained from zone 2, at least one means 10 for recycling from the outlet of zone 3 to the inlet of zone 1 and at least one means 13 for purging optionally present isobutane, whereby said zone also comprises at least one catalyst bed that preferably comprises alumina and titanium.
Figure 2:
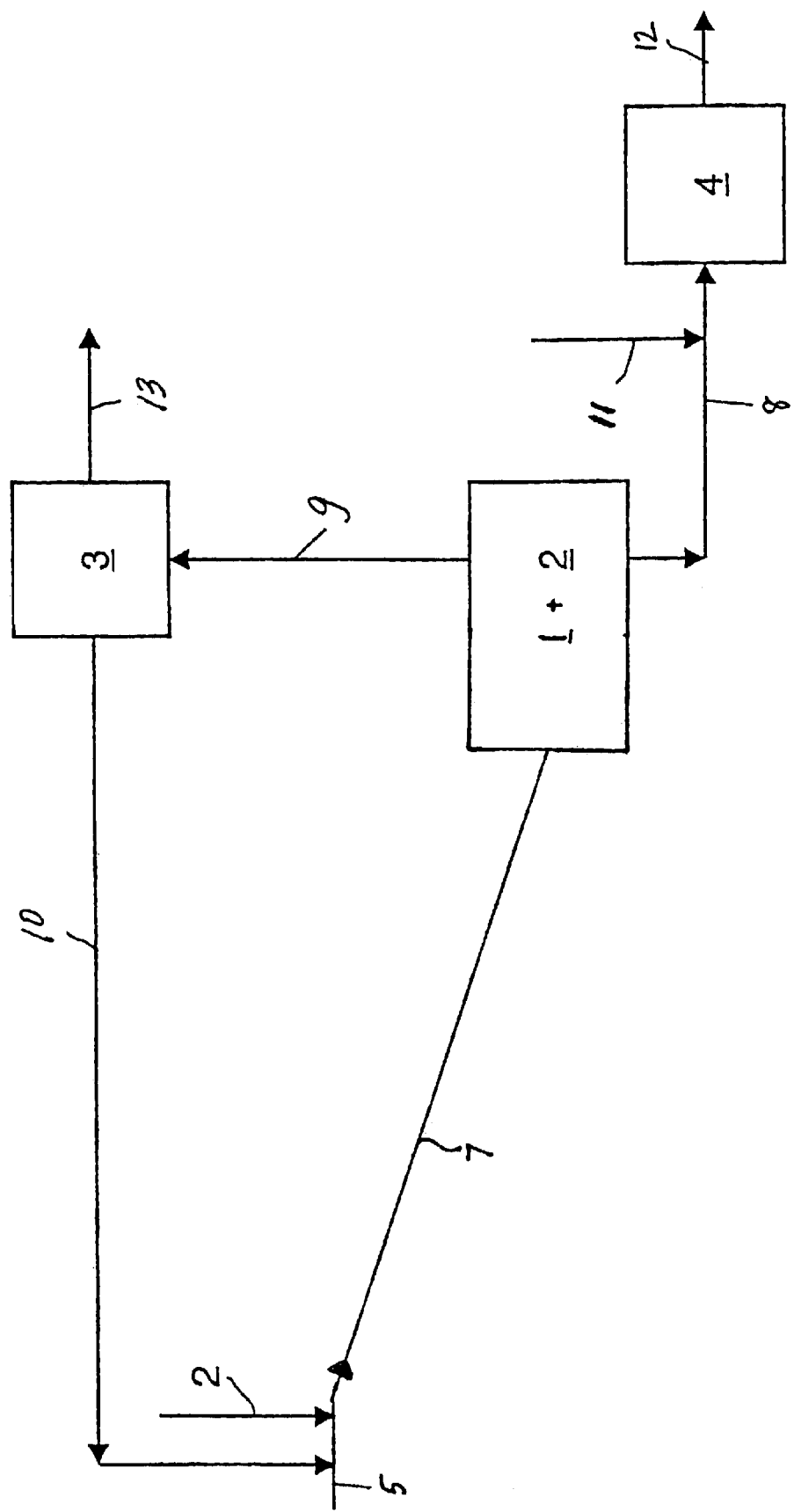
FIG. 2 represents the embodiment of the invention where isomerization and separation are combined into a reactive distillation zone.
Figure 3:
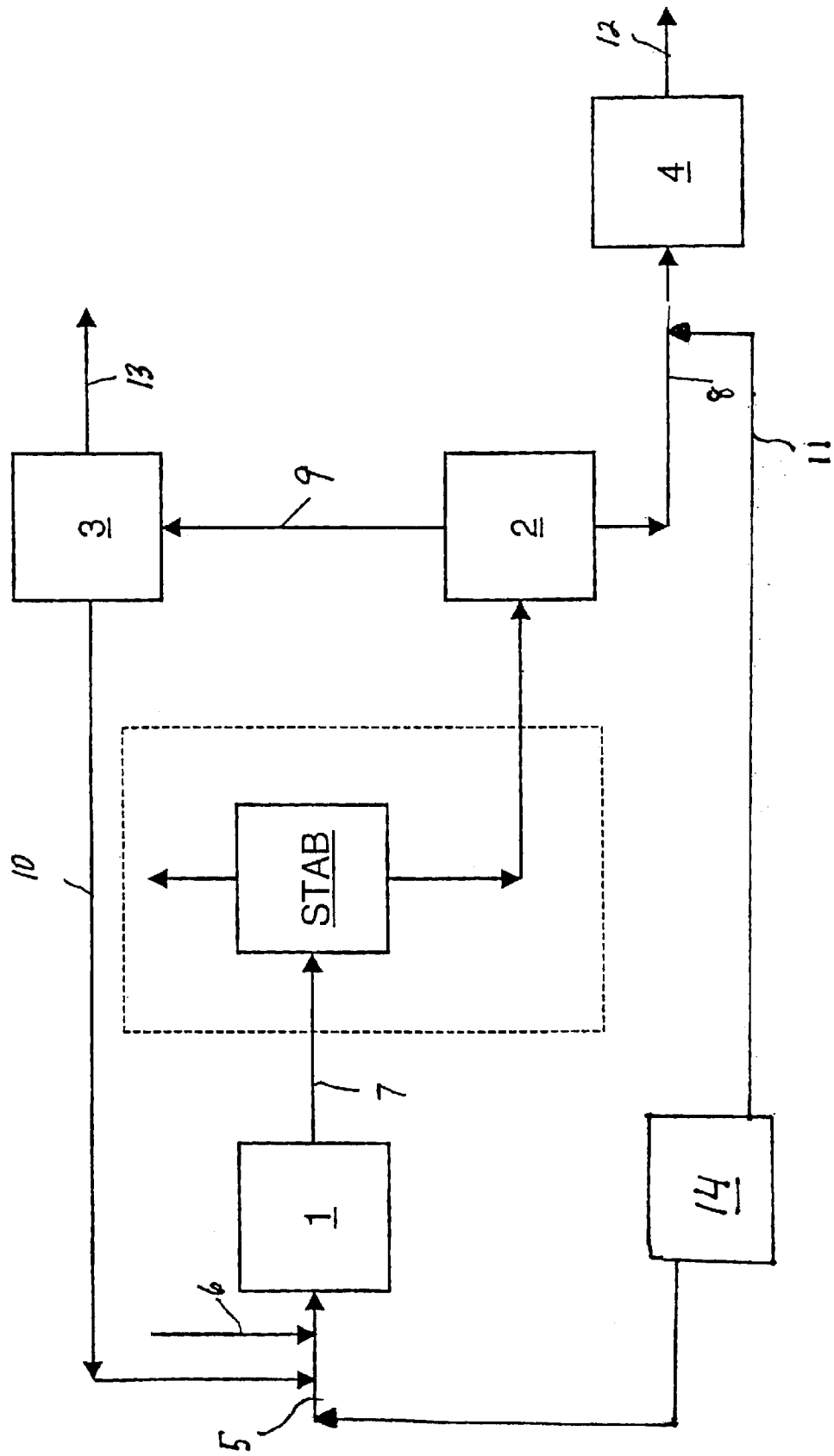
FIG. 3 represents an embodiment of the invention where feed to the isomerization and metathesis zones come from a stream-cracking zone.

In a particularly advantageous way, as shown in FIG., the $C_4$ fraction is obtained from an upstream steam-cracking zone 14, whereby the means 5 for introducing the fraction that is to be converted into zone 1 is connected to said steam-cracking zone, and the means 11 for introducing the ethylene into zone 4 is connected to said steam-cracking zone.

The following example illustrates the invention without limiting its scope.

EXAMPLE

A $C_4$ fraction at the outlet of the steam-cracking device has the composition that is indicated in Table 1 (flow 5). In this table, the abbreviations have the following meanings:

MAPD=methylacetylene+propadiene,

BBV=butadiene-1,2+butyne-1+vinylacetylene.

The $C_4$ fraction that is to be treated is first mixed with flow 10 for recycling the effluent of zone 3 (skeletal isomerization), then it is subjected to a hydrogenation and hydroisomerization treatment in zone 1. It is introduced continuously, with the mass flow rate indicated in Table 1, and under a pressure of 1.4 MPa, in a first reactor that comprises a fixed bed of a catalyst that consists of palladium on alumina that was sulfurized in advance. Hydrogen (mixed with methane) is also injected into this reactor, as indicated in Table 1 (flow 5+10). The effluent of this first reactor is then treated in a finishing reactor that is loaded with the same catalyst. At the outlet (Table 1, flow 7), acetylenic compounds are removed from the fraction, and the butadiene was transformed essentially into butenes, which are for the most part butenes-2, butene-1 having been isomerized. The fraction is then treated in a stabilization column, where the residual hydrogen and the methane are separated.

In zone 2, the hydroisomerized $C_4$ fraction (effluent of zone 1) is subjected to a fractionation in a distillation column. This column comprises about 90 plates and operates at a pressure of 0.7 MPa in the reflux flask so as to allow the use of cooling water in the top condenser. The reflux rate is adjusted, on the one hand, to limit the loss of butene-2 in the distillate, and, on the other hand, to reduce the contents of butene-1 and isobutene in the bottom product to limit to the maximum the formation of pentene and hexene by-products in the subsequent metathesis stage. Top flow 9 from distillation is directed toward skeletal-isomerization zone 3, and bottom flow 8 of distillation is directed toward metathesis zone 4. These two flows have the composition that is given in Table 1.

In zone 3, the catalyst that is used for the skeletal-isomerization reaction of the isobutene consists of gamma-alumina that contains 0.1% by weight of titanium. It was subjected to a treatment under water vapor at 560° C. for 20 hours with a partial water vapor pressure that is equal to 0.08 MPa. It is used to isomerize the isobutene that exits from zone 2 (flow 9) at a temperature of 500° C., a pressure of 0.1 MPa, a water/isobutene molar ratio that is equal to 2 and a volumetric flow rate of 1.3 $h^{-1}$. Under these conditions, the conversion of isobutene is 57% by weight, and the n-butene selectivity is 90%. The effluent of zone 3 is separated into a recycling flow 10 to hydroisomerization zone 1 and a flow 9 that is a purge that is intended to avoid the accumulation of the isobutane that is present in the feedstock fraction. The composition of these two flows is provided in Table 1.

In zone 4, the bottom distillation fraction that contains mainly butene-2 (flow 8) is reacted with ethylene (overall composition: flow 8+11 of Table 1) in a metathesis catalyst that consists of rhenium oxide on gamma-alumina (8% by weight of metal rhenium), prepared according to the teachings of U.S. Pat. No. 4,795,734. The $C_4$ fraction is mixed at the inlet of the metathesis reactor with the make-up ethylene, as well as with recycling flows of ethylene and butenes. This reactor operates in a moving bed, as described in Patent FR-B-2 608 595, at a temperature of 35° C. and under a pressure of 3.5 MPa, and it is coupled with a regenerator that operates at 550° C. under atmospheric pressure. The catalyst is drawn off at regular time intervals at the bottom of the reactor and transferred to the regenerator, from which it is sent to the top of the reactor, whereby the transfers were made through buffer locks. At the outlet of the reactor, the unconverted ethylene is fractionated in a first distillation column and recycled. A second distillation column separates the propylene and the unconverted $C_4$ hydrocarbons that are also recycled. The composition of the metathesis effluent is indicated in Table 1, flow 12.

The overall balance of the transformation is therefore found to be as follows. Per 100 parts by weight (pp) of the $C_4$ fraction that has left the steam-cracking device, 1.6 pp of hydrogen and 44 pp of ethylene are consumed, and 118 pp of propylene is produced. At the steam-cracking device from which is obtained the treated $C_4$ fraction, this balance therefore represents a modest ethylene consumption and a significant additional propylene production.

The advantage of this process is therefore to produce in a very selective way a polymerization-quality propylene in particular with the metathesis of a butene-2 feedstock that contains only small amounts of butene-1 and isobutene, a feedstock that is obtained by hydroisomerization and skeletal isomerization of a $C_4$ fraction, which makes it possible to enhance all of the olefins of this fraction in terms of propylene.

TABLE 1

| Flow No (FIG. 1) (kg/h) | 5 C4 Feedstock | 5 + 10 Hydro-Isomerization Inlet | 7 Hydro-Isomerization Outlet | 8 Stabilization Outlet | 9 Isobutene Column Head | 10 Butenes Recycling | 13 Butenes Purge | 8 Isobutene Column Bottom | 8 + 11 Metathesis Inlet | 12 Metathesis Outlet |
|---|---|---|---|---|---|---|---|---|---|---|
| (C3 + C3)= | 10 | 10 | 41 | | | | | | | |
| MAPD | 31 | 31 | | | | | | | | |
| Isobutane | 446 | 6424 | 6424 | 6424 | 6424 | 5978 | 446 | | | |
| n-Butane | 545 | 545 | 988 | 988 | | | | 988 | 988 | 988 |
| Isobutene | 5741 | 9588 | 9588 | 9588 | 9588 | 3847 | 287 | | | |
| Butene-1 | 3407 | 6455 | 1423 | 1423 | 1312 | 3048 | 238 | 111 | 111 | 89 |
| Butenes-2 | 2250 | 4990 | 18095 | 18095 | | 2740 | 198 | 18095 | 18095 | 1810 |
| Butadiene-1,3 | 8095 | 8095 | | | | | | | | |
| BBV | 104 | 104 | | | | | | | | |
| Hydrogen | | 343 | 26 | | | | | | | |
| Methane | | 197 | 197 | | | | | | | |
| Ethylene | | | | | | | | | 9048 | 845 |
| Propylene | | | | | | | | | | 24428 |

TABLE 1-continued

| Flow No (FIG. 1) (kg/h) | 5 C4 Feed-stock | 5 + 10 Hydro-Isomerization Inlet | 7 Hydro-Isomerization Outlet | 8 Stabilization Outlet | 9 Isobutene Column Head | 10 Butenes Recycling | 13 Butenes Purge | 8 Isobutene Column Bottom | 8 + 11 Metathesis Inlet | 12 Metathesis Outlet |
|---|---|---|---|---|---|---|---|---|---|---|
| Heavy Products | | 504 | 504 | 504 | | 504 | 38 | 504 | 504 | 586 |
| TOTAL | 20629 | 37286 | 37286 | 37022 | 17324 | 16117 | 1207 | 19698 | 28746 | 28746 |

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 99/16.506, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An apparatus for the conversion of an olefinic $C_4$ fraction into isobutene and into propylene, successively comprising:

1) a selective hydrogenation zone with isomerization of butene-1 into butene-2, whereby said zone comprises at least one means (5) for introducing the $C_4$ fraction that is to be converted, at least one means (7) for the output of the effluent and at least one means (6) for the introduction of hydrogen, whereby said selective hydrogenation zone (1) also comprises at least one catalyst bed;

2) a separation that comprises at least one means (7) for introducing the effluent that is obtained from zone (1), at least one means (9) for the output of isobutene and butene-1, at least one means (8) for the output of butene-2 and n-butane; and 4) a metathesis zone that contains at least one catalyst bed and that comprises at least one means (8) for introducing output of butene-2 and n-butane that is obtained from zone (2), at least one means (11) for introducing ethylene and at least one means (12) for the output of propylene, whereby said apparatus also comprises a skeletal-isomerization zone (3) that comprises at least one means (9) for introducing the output of isobutane and butene-1 obtained from zone (2), at least one means (10) for recycling from the outlet of zone (3) to the inlet of zone (1) and at least one means (13) for purging the optionally present isobutane, whereby said skeletal-isomerization zone (3) also comprises at least one catalyst bed.

2. An apparatus according to claim 1, wherein the metathesis zone contains a catalyst moving bed.

3. An apparatus according to claim 2, wherein the means for introducing the $C_4$ fraction that is to be converted is connected to a steam-cracking zone and wherein the means for introducing ethylene into the metathesis zone is connected to said steam-cracking zone.

4. An apparatus according to claim 1, wherein the means (5) for introducing the $C_4$ fraction that is to be converted is connected to a steam-cracking zone (14) and wherein the means (8) for introducing ethylene into the metathesis zone is connected to said steam-cracking zone.

5. An apparatus according to claim 1, wherein the isomerization of butene-1 into butene-2 that is carried out in zone (1) and the separation of zone (2) are conducted in a single zone which is a reactive distillation column that includes on the inside or outside an isomerization catalyst as described for zone (1).

* * * * *